United States Patent [19]

Igarashi et al.

[11] Patent Number: 4,903,703
[45] Date of Patent: Feb. 27, 1990

[54] CONVERSATION DEVICE OF MR IMAGING APPARATUS

[75] Inventors: Yoshiki Igarashi; Tuyosi Shudo, both of Katsuta, Japan

[73] Assignee: Hitachi, Ltd., Tokyo, Japan

[21] Appl. No.: 195,296

[22] Filed: May 18, 1988

[30] Foreign Application Priority Data

May 19, 1987 [JP] Japan .................. 62-121600

[51] Int. Cl.$^4$ ............................... A61B 5/05
[52] U.S. Cl. ................ 128/653 A; 381/151; 381/169; 324/318
[58] Field of Search ........... 128/653, 739; 324/307, 324/309, 318, 322, 300; 381/151, 163, 169, 158

[56] References Cited

U.S. PATENT DOCUMENTS

| | | | |
|---|---|---|---|
| 3,134,861 | 5/1964 | Dempsey et al. | 381/151 |
| 3,787,641 | 1/1974 | Santori | 381/151 |
| 4,025,734 | 5/1977 | Aloupis | 381/183 |
| 4,039,999 | 8/1977 | Weston | 367/132 |
| 4,214,215 | 7/1980 | Mellen et al. | 330/297 |
| 4,309,575 | 1/1982 | Zweig et al. | 381/151 |
| 4,681,098 | 7/1987 | Lee | 128/630 |
| 4,689,565 | 8/1987 | Kemner et al. | 324/318 X |

FOREIGN PATENT DOCUMENTS 2846859  5/1979  Fed. Rep. of Germany ...... 128/739

*Primary Examiner*—Ruth S. Smith
*Attorney, Agent, or Firm*—Antonelli, Terry & Wands

[57] ABSTRACT

The conversation device of an MR imaging apparatus including a magnet for generating a static magnetic field, a gradient field coil disposed between pole pieces of the magnet and used for endowing an NMR signal with positional information, a high-frequency coil disposed in the gradient field coil for transmitting an electromagnetic wave and for detecting the NMR signal, and a bed disposed in the high-frequency coil for holding a person to be inspected, is disclosed. In this conversation device, a bone conduction microphone insensitive to a magnetic field and surrounding noise is mounted on an auxiliary member (which is used for placing the to-be-inspected person at a predetermined position on the bed) so that the bone conduction microphone can be kept in contact with that part of the to-be-inspected person which can conduct the voice of the to-be-inspected person by a bone.

8 Claims, 3 Drawing Sheets

CONVERSATION DEVICE OF MR IMAGING APPARATUS

BACKGROUND OF THE INVENTION

The present invention relates to the conversation device of an MR imaging apparatus, and more particularly to the conversation device of an MR imaging apparatus capable of carrying out conversations between a person to be inspected who is placed in a static magnetic field which produces a harsh noise, and an operator who is placed outside of the static magnetic field.

The conversation device of a conventional MR imaging apparatus employs a microphone which is operated by the vibration of air, in order for a to-be-inspected person who is placed in the static magnetic field of the MR imaging apparatus in a state that the to-be-inspected person lies on his or her back, to talk to an operator placed in an operation room.

The above-mentioned prior art, however, has the following drawback. A large current is instantaneously supplied to a coil which is placed in the static magnetic field of the MR imaging apparatus to generate a gradient magnetic field, and thus the coil vibrates. Noise generated by the vibration of the coil is propagated together with the voice of the to-be-inspected person. Further, even when the to-be-inspected person does not talk, the noise due to the vibration of the coil is propagated.

Since the to-be-inspected person is placed in a magnetic field, a microphone utilizing electromagnetic action is disadvantageous in that the microphone is affected by the magnetic field. A condenser microphone is advantageous in that the microphone is not affected by a magnetic field, but such a microphone cannot remove noise due to the vibration of a coil for generating a gradient magnetic field.

A microphone insensitive to surrounding noise has been known which is called a bone conduction microphone. In more detail, the skull of a person is vibrated by the voice of the person, and the vibration of the skull is detected by the bone conduction microphone inserted into an earhole. Alternatively, the vibration of the nasal bone due to the voice of a person is detected by the bone conduction microphone mounted on the frame of spectacles. Such a voice detecting system and bone conduction microphone are described in a catalog of articles for sale of Pilot Electronics Co. Ltd., by the name of a wireless guide system or ear communication system and an eyeglass microphone. The present inventors have made tests of such a bone conduction microphone, and have confirmed that the bone conduction microphone is not affected by a magnetic field.

The bone conduction microphone inserted into an earhole, however, has the following drawbacks. That is, a person to be inspected may forget to insert the microphone into an earhole of the person. Further, the microphone may slip out of the earhole in the course of inspection.

SUMMARY OF THE INVENTION

It is an object of the present invention to provide the conversation device of an MR imaging apparatus capable of propagating the voice of a person to be inspected, in a favorable manner.

It is another object of the present invention to provide the conversation device of an MR imaging apparatus capable of attaching a bone conduction microphone, which is insensitive to surrounding noise and is not affected by a magnetic field, surely to a person to be inspected.

In order to attain the above objects, according to the present invention, an auxiliary member for placing a to-be-inspected person at a predetermined position in the static magnetic field of an MR imaging apparatus is set on that portion of the upper half part of the to-be-inspected person which can conduct the voice of the to-be-inspected person by a bone, and a bone conduction microphone is fixed to the auxiliary member so that the bone conduction microphone can be pressed against the above portion of the to-be-inspected person.

Thus, the bone conduction microphone is kept surely in contact with that portion of the to-be-inspected person which can conduct the voice of the person by a bone, and hence the voice of the to-be-inspected person can be propagated to a pickup without being affected by a magnetic field and surrounding noise such as the noise due to the vibration of a coil for generating a gradient magnetic field.

DESCRIPTION OF THE PREFERRED EMBODIMENTS

Figure 1:
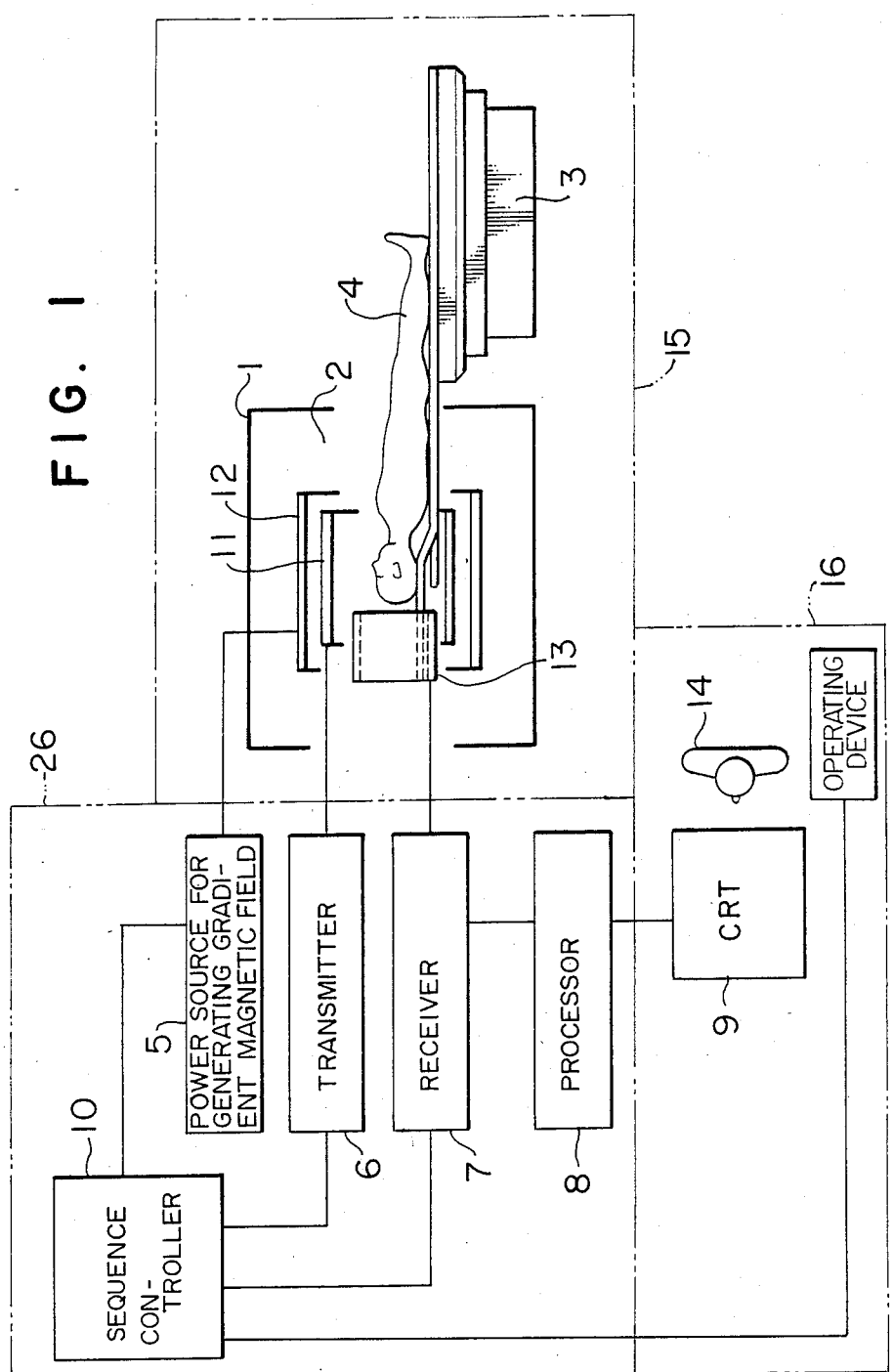
FIG. 1 is a diagram showing an MR imaging apparatus and the positional relation between the MR imaging apparatus and a person to be inspected.

FIG. 1 shows an MR imaging apparatus, to which a conversation device according to the present invention is added.

Referring to FIG. 1, a person 4 to be inspected is placed in a static magnetic field 2 generated by a magnet 1 so that the person 4 lies on his or her back, and a transmitting coil 11 disposed in the neighborhood of the to-be-inspected person 4 is driven by a transmitter 6 for generating a high-frequency magnetic field necessary for nuclear magnetic resonance. Further, gradient field coils 12 arranged on a cylinder are driven by a power source 5 for gradient magnetic fields so that gradient magnetic fields in three directions perpendicular to one another are generated independently of one another. A nuclear magnetic resonance signal generated by the to-be-inspected person 4 is detected by a receiver 7 through a receiving coil 13. The contents and timing of the operation of each of the transmitter 6, the power source 5 for generating gradient magnetic fields, and the receiver 7 are controlled by a sequence controller 10 via an operating device, for example, operated by operator 14. The output of the receiver 7 is digitized and subjected to image reconstruction processing by a processor 8. A reconstructed image from the processor 8 is displayed by a CRT display device 9.

The to-be-inspected person 4 is placed in the static magnetic field 2 in a state that the person 4 lies on a bed 3. The MR imaging apparatus is operated by the operator 14.

The magnet 1 and the bed 3 are disposed in a measuring room 15, and the power source 5, the transmitter 6, the receiver 7, the processor 8 and the controller 10 are placed in a machine room 26. Further, the display device 9 is placed in an operation room 16, and the operator 14 in the operation room 16 operates the MR imaging apparatus.

The present invention relates to a conversation device suitable for use in the MR imaging apparatus having the above-mentioned construction. According to the present invention, a bone conduction microphone necessary for the to-be-inspected person 4, which lies on his or her back at an imaging place in the static magnetic field 2, to speak to the operator 14 in the operation room 16, is incorporated in the MR imaging apparatus.

Figure 2:
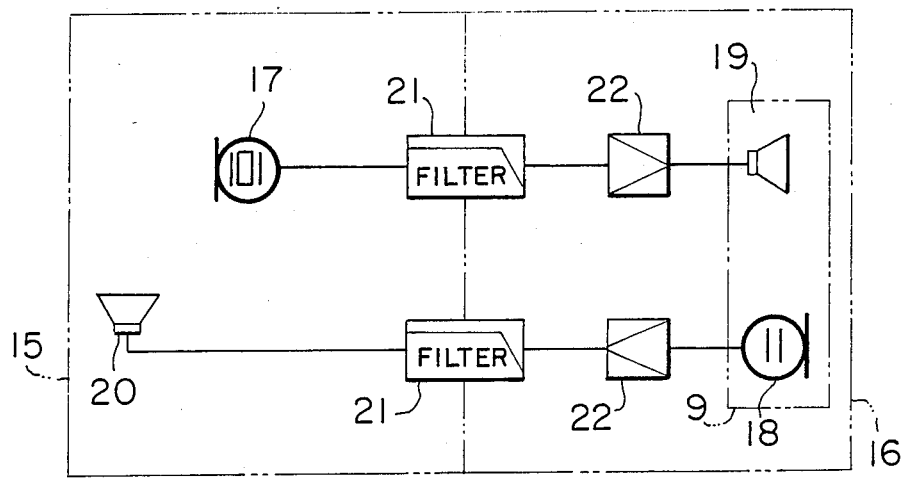
FIG. 2 is a block diagram showing a communication system which includes a bone conduction microphone.

FIG. 2 is a block diagram showing an example of the conversation system (that is, communication system) of the MR imaging apparatus, in which system a bone conduction microphone is incorporated in the MR imaging apparatus.

Referring to FIG. 2, the voice of the to-be-inspected person 4 is picked up by a bone conduction microphone 17. A voice signal from the microphone 17 is sent from the measuring room 15 to the operation room 16 through a filter 21, to be amplified by an amplifier 22. The output of the amplifier 22 is applied to a speaker 19 disposed in the display device 9, to be delivered as a voice. Incidentally, the filter 22 prevents high-frequency noise from entering the measuring room 15.

The voice of the operator 14 is picked up by a console microphone 18. The output of the console microphone 18 is amplified by another amplifier 22. The output of the amplifier is sent from the operation room 16 to the measuring room 15 through another filter 21, to be delivered from a speaker 20 which is disposed in the neighborhood of the to-be-inspected person 4, as a voice.

Figure 3:
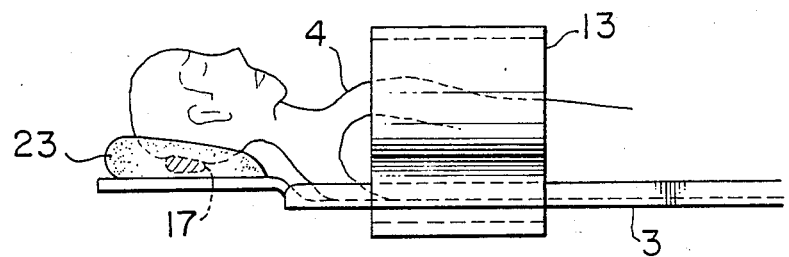
FIG. 3 is a schematic diagram showing an embodiment of the present invention, in which embodiment a bone conduction microphone is mounted on a headrest.

FIG. 3 shows an embodiment of the present invention, in which embodiment the bone conduction microphone 17 is mounted on the headrest 23 of the bed 3. The bone conduction microphone 17 has a thickness of 3 to 5 mm and a bottom area of about 5 mm × 10 mm, that is, has the form of a flat plate, and is bonded to the upper surface of the headrest 23 which is formed by enclosing a sponge with vinyl leather, by an adhesive agent.

Figure 4:
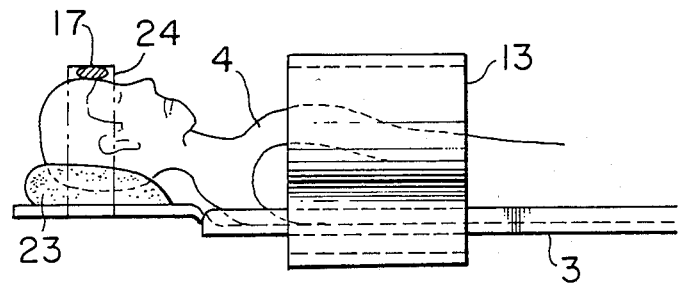
FIG. 4 is a schematic diagram showing another embodiment of the present invention, in which embodiment a bone conduction microphone is mounted on a head fixing band.

FIG. 4 shows another embodiment of the present invention, in which embodiment the bone conduction microphone 17 is bonded to that surface of a head fixing band 24 which faces the head of the to-be-inspected person 4, by an adhesive agent. The head fixing band 24 is formed in such a manner that two sheets of vinyl leather are piled and ridges of the laminate thus obtained are sewed by a sewing machine. Preferably, one end of the band 24 is connected by a fastener. When the head of the to-be-inspected person 4 is fixed by the band 24, the bone conduction microphone 17 is kept in close contact with the forehead of the to-be-inspected person 4, as shown in FIG. 4.

Figure 5:
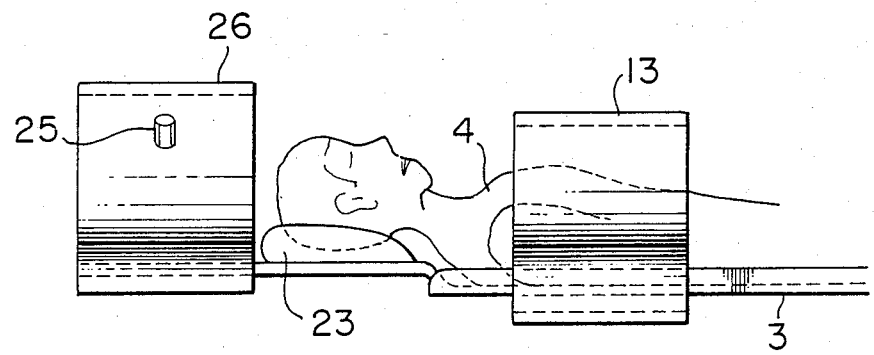
FIG. 5 is a schematic diagram showing a further embodiment of the present invention, in which embodiment a bone conduction microphone is mounted on a head fixing arm.
Figure 6:
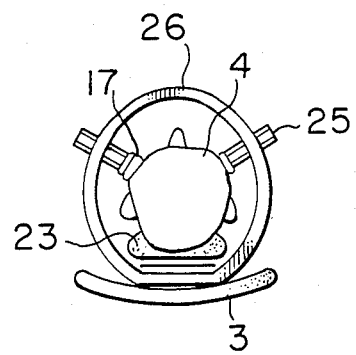
FIG. 6 is a schematic diagram which shows a state that the bone conduction microphone mounted on the head fixing arm of FIG. 5 is kept in contact with the head of a person to be inspected, viewed from the top of the head of the to-be-inspected person.

FIGS. 5 and 6 show a further embodiment of the present invention, in which embodiment the bone conduction microphone 17 is mounted on a head fixing arm for fixing the head of the to-be-inspected person 4. In more detail, FIG. 5 shows a state that a head fixing frame 26 is removed from the head of the to-be-inspected person 4, and FIG. 6 shows a state that the head of the to-be-inspected person 4 is encircled with the head fixing frame 26. In order to encircle the head of the person 4 with the head fixing frame 26, the frame 26 is slided along a holding plate from the position shown in FIG. 5.

The head fixing arm 25 is threaded through the frame 26, and thus the bone conduction microphone 17 mounted on the tip of the arm 25 can be pressed against the forehead of the to-be-inspected person 4.

Although a state that the forehead of the to-be-inspected person 4 is fixed by the arm 25 is shown in FIG. 6, a cheekbone of the person 4 can be fixed by changing the position of the arm 25.

The bone conduction microphone 17 is required to be kept in contact with a bone which is included in one of the head, neck and chest of the person 4, and moreover exists in the neighborhood of the vocal cords. Further, the bone conduction microphone 17 includes conductive members such as a lead wire, and hence it is desirable to mount the bone conduction microphone 17 at a position spaced apart from a measured part. FIGS. 3 to 6 show a case where the chest of the to-be-inspected person 4 is measured, and the bone conduction microphone 17 is pressed against the head of the person 4.

The bone conduction microphone 17 used in the above embodiments does not pick up the vibration of air due to the voice of the to-be-inspected person 4, but detects the vibration of a bone at the head of the person 4 caused by the voice of the person. That is, the microphone 17 picks up only the voice which is propagated by the bone, and hence is insensitive to noise such as the tap-tap generated by the gradient field coil 12. Thus, the operator 14 can hear only the voice of the to-be-inspected person 4 clearly.

According to the above embodiments, it is not required to mount the bone conduction microphone 17 on the to-be-inspected person 4. That is, when the headrest 23 is mounted with the microphone 17, the microphone 17 is naturally pressed against the back part of the head. When the head fixing band 24 is mounted with the microphone 17, the microphone is automatically pressed against the forehead of the to-be-inspected person 4 by fixing the head of the person 4 by the head fixing band 24. Further, when the head fixing arm 25 is provided with the microphone 17, the microphone 17 is automatically pressed against the head of the to-be-inspected person 4 by fixing the head of the person 4 by the head fixing arm 25.

The bone conduction microphone 17 may be attached to one of the bridge of nose, the Adam's apple and the forehead which have a thin skin and can conduct a vocal vibration well, with the aid of a sticking plaster, or may be inserted into an earhole. In this case, however, it is necessary to attach the bone conduction microphone to the to-be-inspected person 4, and the above attachment may be forgotten. Further, the to-be-inspected person 4 may feel uncomfortable when the bone conduction microphone is inserted into an earhole or attached to the person 4 by a sticking plaster. Furthermore, the bone conduction microphone may slip out of the earhole, or may be detached from the to-be-inspected person 4. As is evident from the above, the embodiments shown in FIGS. 3 to 6 are far superior to the prior art.

We claim:

1. A magnetic resonance imaging apparatus provided with a conversation device, comprising:
   a magnet for generating a static magnetic field;
   a gradient field coil disposed between a pair of pole pieces of the magnet for generating a gradient magnetic field, the gradient magnetic field being used for endowing a nuclear magnetic resonance signal with positional information;
   high-frequency transmitting and receiving coils disposed in the gradient field coil for transmitting an electromagnetic wave and for detecting the nuclear magnetic resonance signal, respectively;
   means for forming a magnetic resonance image based on the nuclear magnetic resonance signal;
   bed means, disposed in the high-frequency transmitting and receiving coils, for holding a person to be inspected by the magnetic resonance imaging apparatus;
   an auxiliary member mounted on the bed means for keeping a portion of the to-be-inspected person in a predetermined position on the bed means; and
   a communication system for realizing a conversation between the to-be-inspected person and an operator of the magnetic resonance imaging apparatus, the communication system including:
   a bone conduction microphone mounted on the auxiliary member so that the bone conduction microphone can be kept in contact with that portion of an upper half part of the to-be-inspected person which can conduct the voice of the to-be-inspected person by a bone, the bone conduction microphone being substantially insensitive to a magnetic field and surrounding noise.

2. A magnetic resonance imaging apparatus according to claim 1, wherein the auxiliary member includes a headrest means for holding the head of the to-be-inspected person.

3. A magnetic resonance imaging apparatus according to claim 1, wherein the auxiliary member includes a band means for fixing the head of the to-be-inspected person in a predetermined position on the bed means.

4. A magnetic resonance imaging apparatus according to claim 1, wherein the auxiliary member includes a forehead fixing means for fixing the position of the forehead of the to-be-inspected person, the bone conduction microphone being mounted on a tip of a forehead fixing arm of the forehead fixing means.

5. A magnetic resonance imaging apparatus according to claim 1, wherein the bone conduction microphone is formed in a substantially flat shape.

6. A magnetic resonance imaging apparatus according to claim 1, wherein the bone conduction microphone is mounted on a surface of the auxiliary member by an adhesive agent.

7. A magnetic resonance imaging apparatus according to claim 1, wherein the communication system further includes means for preventing high-frequency noise from entering that portion of the static magnetic field where the to-be-inspected person is placed.

8. A magnetic resonance imaging apparatus according to claim 7, wherein the means for preventing comprises a filter.

* * * * *